United States Patent [19]

Koch et al.

[11] Patent Number: 5,120,529
[45] Date of Patent: Jun. 9, 1992

[54] WATER-BASED NAIL POLISH

[75] Inventors: Detlef Koch; Richard Rassek, both of Hamburg, Fed. Rep. of Germany

[73] Assignee: Cosmolab, Inc., Lewisburg, Tenn.

[21] Appl. No.: 592,989

[22] Filed: Oct. 4, 1990

[51] Int. Cl.$^5$ .............................................. A61K 7/043
[52] U.S. Cl. ......................................... 424/61; 424/59
[58] Field of Search ............................ 424/61; 524/591

[56] References Cited

U.S. PATENT DOCUMENTS

| 4,155,892 | 5/1979 | Emmons et al. | 524/591 |
| 4,649,045 | 3/1987 | Gaske | 424/61 |
| 4,712,571 | 12/1987 | Remz | 424/61 |

FOREIGN PATENT DOCUMENTS 0143480  5/1985  European Pat. Off.
3931237  6/1990  Fed. Rep. of Germany.

OTHER PUBLICATIONS

Remz, Polymers and Thickeners in Nail-Care Products, Cosmetics and Toiletries; vol. 103:70, Dec. 1988, pp. 70-82.

Primary Examiner—Thurman K. Page
Assistant Examiner—D. Colucci
Attorney, Agent, or Firm—Fitzpatrick, Cella, Harper & Scinto

[57] ABSTRACT

A water-based nail polish, which comprises 12 to 50 percent by weight of polyurethane and/or a polyurethane copolymer in dispersed form as a binder, 0.1 to 1 percent by weight of a thickener and water as well as further additives, as required.

15 Claims, No Drawings

WATER-BASED NAIL POLISH

BACKGROUND OF THE INVENTION

1. Field of the Invention

The invention relates to a water-based nail polish.

2. Brief Description of the Prior Art

Known nail polish on the basis of organic solvents has the disadvantage that the solvents attack the nails in the course of repeated usage and may damage them. Additionally, released solvent vapors are inhaled during application and drying, which may pose dangers to health. Finally, with a view of preserving the environment, it is also desirable to avoid organic solvents wherever possible. For all of these reasons there is a need for replacing solvent-containing nail polish by water-based nail polish.

A nail polish preparation consisting of a watery polymer emulsion is described in German Published, Non-examined Patent Application DE-OS 27 57 773. Preparation takes place by watery emulsion polymerization of two or more monomers selected from acrylate, methacrylate or styrene monomers. At least one of the selected monomers must be an acrylate or methacrylate.

A cosmetic preparation for strengthening the nails is known from German Patent DE-PS 28 54 337. In accordance with one embodiment, it contains trimethylolamine in a watery solution, at least one non-cationic resin and/or at least one cationic cosmetic resin, at least one softener and an organic or inorganic acid. This composition is not a nail polish.

An ink-like nail polish is described in German Published, Non-examined Patent Application DE-OS 32 47 172. It comprises a polyester resin soluble in alkali, ammonia, a cosmetically acceptable acidic organic coloring agent, additives and water.

These few known compositions are unable to satisfy the demands of users in every way.

SUMMARY OF THE INVENTION

It is therefore the object of the invention to provide a nail polish with improved properties.

The object is attained by means of a water-based nail polish which consists of 12 to 50 percent by weight of polyurethane and/or a polyurethane copolymer in dispersed form as binder, 0.1 to 1 percent by weight of a thickener and water, as well as water-soluble, natural and/or synthetic resins, colorants, surfactants, drying accelerators and/or further additives, if desired.

Polyurethanes and polyurethane copolymers suitable in accordance with the invention are commercially available in the form of watery, finely dispersed plastic dispersions. Typically the commercial products have a solid matter content of 30 to 50 percent by weight. Based on such commercial products, the binder content of the desired water-based nail polish can be adjusted by thinning it with water. In accordance with the invention, a watery dispersion on the basis of linear polyurethane is particularly preferred. A polyurethane-acrylate copolymer is preferred as polyurethane copolymer.

The water-based nail polish according to the invention contains 0.1 to 1 percent by weight of a thickener as a further required component. Examples of the thickeners are natural rubbers, such as guar gum, gum arabic, cellulose and cellulose derivatives, silicates, clays and synthetic polymers such as acrylates. Hydrophilic montmorillonite, for example, is usable as a clay thickener and is commercially available under the name Bentone (registered trademark). Acrylate thickeners, in particular acrylate copolymers, are preferred in accordance with the invention.

The properties of the water-based nail polish of the invention can be considerably improved by the addition of one or several water-soluble, natural and/or synthetic resins. The resins cause increased hardness of the dried layer of the nail polish as well as improved adhesion of the layer to the nail. Caoutchouc and shellac are examples of natural resins which are cosmetically acceptable. Examples of synthetic resins suitable in accordance with the present invention are acrylic resins, styrene resins, vinyl resins and acrylate-styrene resins. The preferred resins in accordance with the present invention are acrylate-styrene copolymers, in particular one having a molecular weight above 200,000 and an acid number in the range between 50 to 65. The resins are preferably used in amounts between 2 to 15 percent by weight, in particular 5 to 12 percent by weight and most preferably 10 to 12 percent by weight in relation to the weight of the nail polish.

In most cases a colorant is contained in the nail polish of the present invention. A large number of the colorants used in solvent-containing nail polish also are usable in connection with this invention. Therefore, the selection of the colorants can be made in the known manner, however, care should be taken to see that the colorant is compatible with water. Choice of the colorant is based on whether a transparent, an opaque or an iridescent nail polish is to be manufactured. Organic colorants and pigments, inorganic pigments, pearly luster and fish silver materials may be used. Use of the colorant in the form of a dispersion, for example pigment dispersion, is particularly practical from a technical production point of view. There are also no differences with regard to the required amounts of colorant in comparison to solvent-containing nail polish.

It may be useful in some cases to add to the nail polish of the present invention one or several cosmetically acceptable tensides in amounts up to 1 percent by weight in relation to the weight of the nail polish.

The use of the nail polish in accordance with the invention is made easier if a drying accelerator is added. Suitable drying accelerators are, on the one hand, slowly volatilizing liquids, which are good solvents for the binder and therefore prevent the formation of a skin on the surface of the drying polish layer and, on the other hand, highly volatile liquids, which evaporate together with water. A preferred drying accelerator of the first type in connection with the instant invention is a slowly volatilizing glycol ester, in particular butyl glycol acetate. Preferred drying accelerators of the second type in accordance with the present invention are volatile alcohols, in particular ethanol and/or 2-propanol.

The drying accelerators are preferably used in amounts between 0.1 to 5 percent by weight in relation to the weight of the nail polish.

Modified silicones can be added to the nail polish of the present invention to increase its scratch resistance and to prevent surface blemishes or to increase the smoothness of the surface. A polyether-modified dimethylpolysiloxane copolymer, for example, is suitable for this. Alternatively, it is also possible to use hard waxes for the same purpose. These are commercially available in the form of watery dispersions and are preferably used in this form for manufacturing the nail polish of the present invention.

Furthermore, it may be useful to provide an additive serving to prevent sedimentation of the components of the nail polish, in particular of the pigments. Calcium silicate hydrate is an example of a sedimentation inhibitor suitable in connection with the instant invention.

Of course it is also possible for the nail polish of the present invention to contain substances for the care and protection of the nails. Examples of such substances are proteins, vitamins and sun screen substances.

The nail polish can be made more pleasant to use by the addition of aromatic substances. Finally, its shelf life can be increased by the addition of preservatives.

The invention also relates to the use as nail polish of a watery polyurethane and/or polyurethane copolymer dispersion, and with additives if necessary.

The invention will be described in detail below by means of examples.

DETAILED DESCRIPTION OF THE INVENTION

All amounts in the above description, in the claims and in the examples relate to percent by weight of the total weight of the nail polish. To the extent that components of the nail polish are or can be used in the form of dispersions or solutions, such as binders or colorants, the amounts in percent by weight relate to the content of solids of the components in the finished nail polish.

EXAMPLE 1

Red Creamy Nail Polish

- 36.1% by wt. of polyurethane acrylate copolymer in the form of a finely dispersed dispersion
- 0.45% by wt. of montmorillonite thickener (Bentone LT TM)
- 0.5% by wt. of calcium silicate hydrate $(Ca_6Si_6)_{1.7}(OH)_2$
- 0.06% by wt. of acrylate thickener
- 0.5% by wt. of butyl glycol acetate
- 0.8% by wt. of Pigment White 77891 (Flexonylweiss RLLA TM)
- 0.2% by wt. of Pigment Red 12355 (Unipers Rot RBS-Pi TM)
- 61.39% by wt. of water The polyurethane acrylate copolymer was presented as a finely dispersed watery dispersion and was mixed under intense stirring with the montmorillonite thickener and the calcium silicate hydrate. After adding the acrylate thickener and the butyl glycol acetate, slow stirring was continued until the substance became highly viscous. Subsequently the pigment preparations were worked in while stirring.

The result was a red creamy polish with good suitability as a nail polish.

EXAMPLE 2

Nacreous Pigment Nail Polish

Example 1 was repeated except that in place of the pigments used therein, the following colorants were stirred in:

- 1% by wt. of Pigment White 77019 (Iriodin 120 TM) as nacreous pigment
- 0.2% by wt. of Pigment Red 12355 (Unipers Rot RBS-Pi TM)

The result was a red nacreous nail polish with good suitability as nail polish.

EXAMPLE 3

Red Nail Polish

- 27.2% by wt. of polyurethane as finely dispersed dispersion
- 13.8% by wt. of acrylic copolymer as water dispersion
- 0.08% by wt. of acrylate thickener
- 0.5% by wt. of butyl glycol acetate
- 0.4% by wt. of Pigment Red 12355 (Unipers Rot RBS-Pi TM)
- 58.02% by wt. of water The polyurethane was presented as a finely dispersed watery dispersion. The acrylic copolymer was added in the form of a watery dispersion under stirring. The acrylate thickener was subsequently added under stirring. Stirring was continued until the substance became highly viscous. Subsequently the colorants were stirred in.

The result was a red nail polish with good application properties.

While preferred embodiments of the invention have been described, the invention is to be defined by the appended claims.

What is claimed is:

1. A water-based nail polish consisting essentially of 12 to 50 percent by weight of at least one of a polyurethane and a polyurethane copolymer in dispersed form as a binder based on the total weight of said nail polish, 0.1 to 1 percent by weight of a thickener based on the total weight of said nail polish, said thickener being selected from the group consisting of guar gum, gum arabic, cellulose and cellulose derivatives, silicates, clays and synthetic polymers, to 15 percent by weight based on the total weight of said nail polish of an acrylate-styrene copolymer with a molecular weight above 200,000 and an acid number in the range between 50 to 65, and the balance substantially water.

2. A water-based nail polish in accordance with claim 1, wherein said dispersed polyurethane copolymer is a polyurethane acrylate copolymer.

3. A water-based nail polish in accordance with claim 1, wherein said thickener is an acrylate synthetic copolymer thickener.

4. A water-based nail polish in accordance with claim 1, wherein said thickener is a hydrophilic montorillonite clay thickener.

5. A water-based nail polish in accordance with claim 1, wherein said nail polish further comprises colorants.

6. A water-based nail polish in accordance with claim 1, wherein said nail polish further comprises a slowly volatilizing solvent for the binder as a drying accelerator.

7. A water-based nail polish in accordance with claim 6, wherein said nail polish comprises 0.1 to 5 percent by weight of a slowly volatilizing glycol ester based on the total weight of said nail polish as said drying accelerator.

8. A water-based nail polish in accordance with claim 7, wherein said nail polish comprises butyl glycol acetate as said drying accelerator.

9. A water-based nail polish in accordance with claim 1, wherein said nail polish further comprises 0.1 to 5 percent by weight of a volatile alcohol as a drying accelerator based on the total weight of said nail polish.

10. A water-based nail polish in accordance with claim 9, wherein said nail polish comprises ethanol or 2-propanol as said drying accelerator.

11. A water-based nail polish in accordance with claim 1, wherein said nail polish further comprises a modified silicone for improving scratch resistance of said nail polish.

12. A water-based nail polish in accordance with claim 1, wherein said nail polish further comprises a sedimentation inhibitor.

13. A water-based nail polish in accordance with claim 12, wherein said nail polish comprises calcium silicate hydrate as said sedimentation inhibitor.

14. A water-based nail polish in accordance with claim 1, wherein said nail polish further comprises proteins, vitamins and sun screen substances as cosmetic additives.

15. A water-based nail polish in accordance with claim 1, wherein said nail polish further comprises preservatives.

* * * * *